(12) United States Patent
Kimura

(10) Patent No.: US 7,130,031 B2
(45) Date of Patent: *Oct. 31, 2006

(54) OPTICAL CHARACTERISTICS MEASURING APPARATUS, METHOD AND RECORDING MEDIUM

(75) Inventor: Eiji Kimura, Saitama (JP)

(73) Assignee: Advantest Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/812,014

(22) Filed: Mar. 30, 2004

(65) Prior Publication Data

US 2004/0179189 A1    Sep. 16, 2004

Related U.S. Application Data

(62) Division of application No. 09/877,202, filed on Jun. 11, 2001, now Pat. No. 6,864,967.

(30) Foreign Application Priority Data

Jun. 15, 2000    (JP) ............................ P2000-179716

(51) Int. Cl.
    *G01N 21/00*    (2006.01)
(52) U.S. Cl. ..................................... 356/73.1
(58) Field of Classification Search ............... 356/73.1, 356/364–367; 250/225, 227.17; 385/11, 385/15, 24, 27, 39, 122; 359/279, 326
    See application file for complete search history.

(56) References Cited

U.S. PATENT DOCUMENTS

| 4,551,019 | A |   | 11/1985 | Vella et al. |
|---|---|---|---|---|
| 4,997,277 | A |   | 3/1991 | Horiguchi et al. |
| 5,278,687 | A |   | 1/1994 | Jannson et al. |
| 5,406,368 | A |   | 4/1995 | Horiuchi et al. |
| 5,969,806 | A |   | 10/1999 | Bergano |
| 5,982,530 | A | * | 11/1999 | Akiyama et al. ........... 359/279 |
| 6,144,485 | A |   | 11/2000 | Sugaya et al. |
| 6,212,003 | B1 |   | 4/2001 | Komazawa et al. |
| 6,504,604 | B1 | * | 1/2003 | Holland ..................... 356/73.1 |
| 6,515,792 | B1 | * | 2/2003 | Hakimi et al. ............... 359/326 |
| 6,594,003 | B1 | * | 7/2003 | Horiuchi et al. ........... 356/73.1 |

FOREIGN PATENT DOCUMENTS

| EP | 0280328 | 8/1988 |
|---|---|---|
| EP | 0 348235 | 12/1989 |
| GB | 2353591 A | 2/2001 |
| WO | WO99/43054 | 8/1999 |

\* cited by examiner

*Primary Examiner*—Tu T. Nguyen
(74) *Attorney, Agent, or Firm*—Lowe Hauptman & Berner, LLP.

(57) ABSTRACT

An apparatus including a variable wavelength light source for generating a variable wavelength light, a first light modulator for inputting into a first optical fiber transmission line a first incident light obtained by modulating the variable wavelength light by a frequency of an electrical signal inputted, a first converter for converting the first incident light, a fixed wavelength light source for generating a fixed wavelength light, a signal source for generating a reference electrical signal, a second light modulator for inputting in a second optical fiber transmission line a second incident light obtained by modulating the fixed wavelength light by a frequency of the reference electrical signal and a second converter for converting the second incident and for outputting the electrical signal into the first light modulator.

10 Claims, 7 Drawing Sheets

OPTICAL CHARACTERISTICS MEASURING APPARATUS, METHOD AND RECORDING MEDIUM

RELATED APPLICATION

This application is a divisional of U.S. patent application Ser. No. 09/877,202, filed Jun. 11, 2001 now U.S. Pat. No. 6,864,967.

BACKGROUND OF INVENTION

1. Field of Invention

The present invention relates to the measurement of the wavelength dispersion characteristic of devices under test (DUT) such as fiber pair, and in particular to the measurement of the wavelength dispersion characteristic by connecting separate measuring methodes on both ends of the DUT.

2. Description of the Related Art

In case of light being transmitted over a long distance, the transmission of light only through an optical fiber will involve considerable losses. Therefore, optical fiber transmission lines combined with optical amplifiers (EDFA) for amplifying optical signals are used for the optical fiber to prevent any possible losses. The optical amplifiers let light through only in one direction. Therefore, a bi-directional communication requires a cable integrating an optical fiber transmission line transmitting light in one direction and another optical fiber transmission line transmitting light in the direction opposite to the one direction. This cable is called a fiber pair.

The configuration of a fiber pair is shown in FIG. 6(a). An optical fiber 112 combined with an optical amplifier 114 constitute an optical fiber transmission line 110. The optical fiber transmission line 110 lets light through to the right. An optical fiber 122 combined with an optical amplifier 124 constitutes an optical fiber transmission line 120. The optical fiber transmission line 120 lets light through to the left. An optical fiber transmission line 110 and a optical fiber transmission line 120 constitutes an optical fiber pair 100a. Incidentally, two sets of fiber pairs are called two fiber pairs as shown in FIG. 6(b). Fiber pairs 100a and 100b constitute two fiber pairs 100.

The configuration of the measurement system for measuring the wavelength characteristic of two fiber pairs is shown in FIG. 7. At one end of a fiber pair 100a, which is one of two fiber pairs 100, a variable wavelength light source 202 is connected and at another end an O/E (optical/electric) converter 302 is connected. At one end of a fiber pair 100b, which is one of the two fiber pairs 100, a fixed wavelength light source 204 is connected, and at another end an O/E (optical/electric) converter 304 is connected. Incidentally, between the variable wavelength light sources 202, 204 and single fiber pairs 100a, 100b, a light modulator may be installed.

To measure wavelength dispersion characteristics, the wavelength λ x of the variable wavelength light source 202 is swept, while the wavelength λ 0 of the fixed wavelength light source 204 is fixed. The phase difference between the output signals of the O/E converter 302 and the output signals of the O/E converter 304 is measured by the phase comparator 306, to measure the wavelength dispersion characteristic of the two fiber pairs.

Here, in a bulk transmission line constituting a trunk line, two fiber pairs may be secured. In most lines already laid out, often only one fiber pair can be secured. Therefore, it is necessary to measure the wavelength dispersion characteristic of a single fiber pair.

SUMMARY OF INVENTION

Such a measuring method of the wavelength dispersion characteristic, however, cannot be applied to a single fiber pair. The reason is that two lines consisting of a line for letting a fixed wavelength light through and another line for letting a variable wavelength light through cannot be secured by a single fiber pair.

Further, even if such a measuring method of wavelength dispersion characteristic is applied to two fiber pairs 100, the measurements may involve errors. In other words, due to physical quantitative variations including variations in the temperature, stress, etc. of the transmission line, the phase difference of light penetrating a fiber pair 100a and another fiber pair 100b may vary due to factors independent of wavelength. In such a case, the measurements may involve errors. Therefore, it is desirable that wavelength dispersion characteristics may be measured only by a single fiber pair without using two fiber pairs.

Therefore, the present invention has an object of providing an apparatus capable of measuring wavelength dispersion characteristic and other characteristics only through a single fiber pair.

According to a first embodiment, an optical characteristic measuring apparatus for measuring the characteristics of devices under test having the first optical transmission line letting light through in one direction only and the second optical transmission line letting light through only on the direction opposite to the aforementioned direction includes: a variable wavelength light source for generating a variable wavelength light, the wavelength of which is variable; a first light modulating unit for introducing into the first optical transmission line the first incident light obtained by modulating the variable wavelength light by the frequency of the electrical signal inputted; a first optical/electrical converting unit for converting by the optical/electrical conversion process the first incident light having penetrated the first optical transmission line; a fixed wavelength light source for generating a fixed wavelength light, the wavelength of which is fixed; a signal source for generating reference electrical signals of given frequencies; a second light modulating unit for injecting into the second optical transmission line the second incident light obtained by modulating the fixed wavelength light by the frequency of the reference electrical signals; and a second optical/electrical converting unit for converting by the optical/electrical conversion process the second outgoing light having penetrated the second optical transmission line; and for outputting the converted second outgoing light onto the first light modulating unit.

According to an optical characteristic measuring apparatus thus configured, once the wavelength of the fixed wavelength light is set in such a way that wavelength dispersion may be small in the second optical transmission line, the result of optical/electrical conversion of the second outgoing light produces a small phase difference than that of the second incident light. Thus, it is possible to consider that the result of optical/electrical conversion of the second outgoing light and the reference electrical signals may have the identical frequencies and phases. Thus, it is possible to consider that the first incident light may be same as the result of modulation of the variable wavelength light by the reference electrical signals. Thus, once the result of optical/ electrical conversion of the first outgoing light and the reference electrical signals are obtained, the comparison of their phases can lead to the discovery of phase differences related to the first optical transmission line. And from the phase difference, wavelength dispersion characteristic and other factors can be computed.

According to a second embodiment, an optical characteristic measuring apparatus for measuring the characteristics of devices under test having the first optical transmission line for letting light through only in one direction and the second optical transmission line for letting light through only in the direction opposite to the one direction includes: a fixed wavelength light source for generating a fixed wavelength light, the wavelength of which is fixed; a first light modulating unit for introducing into the first optical transmission line the first incident light obtained by modulating the fixed wavelength light by the frequency of the electrical signals inputted; a first optical/electrical converting unit for converting by the optical/electrical conversion process the first outgoing light having penetrated the first optical transmission line; a variable wavelength light source for generating a variable wavelength light, the wavelength of which is variable; a signal source for generating reference electrical signals of given frequencies; a second light modulating unit for introducing onto the second optical transmission line the second incident light obtained by modulating the variable wavelength light by the frequency of the reference electrical signals; and a second optical/electrical converting unit for converting by the optical/electrical conversion process the second outgoing light having penetrated the second optical transmission line and for outputting the converted second outgoing light onto the first light modulating unit.

According to an optical characteristic measuring apparatus thus configured, the result of optical/electrical conversion of the second outgoing light will be electrical signals containing phase differences related to the second optical transmission line. Therefore, once the wavelength of the fixed wavelength light is set in such a way that wavelength dispersion may be small in the first optical transmission line, the first outgoing light containing phase differences related to the second optical transmission line and yet free of errors related to the first optical transmission line can be obtained. Thus, once the result of optical/electrical conversion of the first outgoing light and the reference electrical signals are obtained, the comparison of their phases can lead to the discovery of phase difference related to the second optical transmission line. And from the phase difference, wavelength dispersion characteristic and other factors can be computed.

According to a third embodiment, an optical characteristic measuring apparatus for measuring the characteristics of devices under test having the first optical transmission line letting light through only in one direction and the second optical transmission line letting light through only in the direction opposite to the one direction includes: a first variable wavelength light source for generating the first variable wavelength light, the wavelength of which is variable; a first light modulating unit for introducing onto the first optical transmission line the first incident light obtained by modulating the first variable wavelength light by the frequency of electrical signals inputted; a first optical/electrical converting unit for converting by the optical/electrical conversion process the first outgoing light having penetrated the first optical transmission line; a second variable wavelength light source for generating the second variable wavelength light, the wavelength of which is variable; a signal source for generating reference electrical signals of given frequencies; a second light modulating unit for introducing into the second optical transmission line the second incident light obtained by modulating the second variable wavelength light by the frequency of the reference electrical signals; and a second optical/electrical converting unit for converting by the optical/electrical conversion process the second outgoing light having penetrated the second optical transmission line and for outputting the converted second outgoing light onto the first light modulating unit.

According to an optical characteristic measuring apparatus thus configured, by using a first variable wavelength light source and a second variable wavelength light source, the wavelength dispersion characteristic and other factors of the first optical transmission line and the second optical transmission line can be computed.

According to a fourth embodiment, the optical characteristic measuring apparatus according to the second embodiment further includes a third optical/electrical converting unit for converting by the optical/electrical conversion process the reflected light generated when the second light modulating unit introduces the second incident light into the second optical transmission line.

According to a fifth embodinment, the optical characteristic measuring apparatus according to the first embodiment further includes: a phase comparing unit for measuring the phase difference between the electrical signals for measurement outputted by the first optical/electrical converting unit and the reference electrical signals; and a characteristic computing unit for computing the group delay characteristic or the dispersion characteristic of the devices under test by using the phase difference.

According to a sixth embodiment, the optical characteristic measuring apparatus according to the fourth embodiment further includes: a phase comparing unit for measuring the phase difference between the electrical signals for reflection measurement outputted by the third optical/electrical converting unit and the reference electrical signals; and a characteristic computing unit for computing the group delay characteristic or the dispersion characteristic of the devices under test.

According to a seventh embodiment, a light generating apparatus used in an apparatus for measuring the characteristics of devices under test having the first optical transmission line letting light through only in one direction and the second optical transmission line letting light through only on the direction opposite to the one direction includes: a variable wavelength light source for generating a variable wavelength light, the wavelength of which is variable; a first light modulating unit for introducing into the first optical transmission line the first incident light obtained by modulating the variable wavelength light by the frequency of electrical signals inputted; and a second optical/electrical converting unit for converting by the optical/electrical conversion process the second outgoing light having penetrated the second optical transmission line and for outputting the converted second outgoing light onto the first light modulating unit.

According to an eighth embodiment, an optical characteristic measuring apparatus for measuring the characteristics of devices under test having a first optical transmission line letting light through only in one direction and a second optical transmission line letting light through only in the direction opposite to the one direction includes: a first optical/electrical converting unit for converting by the optical/electrical conversion process the first incident light having penetrated the first optical transmission line; a fixed wavelength light source for generating a fixed wavelength light, the wavelength of which is fixed; a signal source for generating reference electrical signals of given frequencies; and a second light modulating unit for introducing into the second optical transmission line the second incident light obtained by modulating the fixed wavelength light by the frequency of the reference electrical signals.

According to an ninth embodiment, a light generating apparatus used in a measuring apparatus of the characteristics of devices under test having the first optical transmission line letting light through only in one direction and the second optical transmission line letting light through only in the direction opposite to the one direction includes: a fixed wavelength light source for generating a fixed wavelength light, the wavelength of which is fixed; a first light modulating unit for introducing into the first optical transmission line the first incident light obtained by modulating the fixed wavelength light by the frequency of electrical signals inputted; and a second optical/electrical converting unit for converting by the optical/electrical conversion process the second outgoing light having penetrated the second optical transmission line and for outputting the converted second outgoing light onto the first light modulating unit.

According to a tenth embodiment, an optical characteristic measuring apparatus for measuring the characteristics of devices under test having the first optical transmission line letting light through only in one direction and the second optical transmission line letting light through only in the direction opposite to the one direction includes: a first optical/electrical converting unit for converting by the optical/electrical conversion process the first outgoing light having penetrated the first optical transmission line; a variable wavelength light source for generating a variable wavelength light, the wavelength of which is variable; a signal source for generating reference electrical signals of given frequencies; a second light modulating unit for introducing into the second optical transmission line the second incident light obtained by modulating the variable wavelength light by the frequency of the reference electrical signals.

According to an eleventh embodiment, a light generating apparatus used in a measuring apparatus of the characteristics of devices under test having the first optical transmission line letting light through only in one direction and the second optical transmission line letting light through only in the direction opposite to the one direction includes: a first variable wavelength light source for generating the first variable wavelength light, the wavelength of which is variable; a first light modulating unit for introducing into the first optical transmission line the first incident light obtained by modulating the first variable wavelength light by the frequency of electrical signals inputted; and a second optical/electrical converting unit for converting by the optical/electrical conversion process the second outgoing light having penetrated the second optical transmission line and for outputting the converted second outgoing light onto the first light modulating unit.

According to a twelfth embodiment, an optical characteristic measuring apparatus for measuring the characteristics of devices under test having the first optical transmission line letting light through only in one direction and the second optical transmission line letting light through only in the direction opposite to the one direction includes: a first optical/electrical converting unit for converting by the optical/electrical conversion process the first outgoing light having penetrated the first optical transmission line; a second variable wavelength light source for generating the second variable wavelength light, the wavelength of which is variable; a signal source for generating reference electrical signals of given frequencies; a second light modulating unit for introducing into the second optical transmission line the second incident light obtained by modulating the second variable wavelength light by the frequency of the reference electrical signals.

According to a thirteenth embodiment, an optical characteristic measuring method for measuring the characteristics of devices under test having the first optical transmission line letting light through in one direction only and the second optical transmission line letting light through only on the direction opposite to the aforementioned direction includes: a variable wavelength light generating step for generating a variable wavelength light, the wavelength of which is variable; a first light modulating step for introducing into the first optical transmission line the first incident light obtained by modulating the variable wavelength light by the frequency of the electrical signal inputted; a first optical/electrical converting step for converting by the optical/electrical conversion process the first incident light having penetrated the first optical transmission line; a fixed wavelength light generating step for generating a fixed wavelength light, the wavelength of which is fixed; a signal generating step for generating reference electrical signals of given frequencies; a second light modulating step for injecting into the second optical transmission line the second incident light obtained by modulating the fixed wavelength light by the frequency of the reference electrical signals; and a second optical/electrical converting step for converting by the optical/electrical conversion process the second outgoing light having penetrated the second optical transmission line; and for outputting the converted second outgoing light onto the first light modulating step.

According to a fourteenth embodiment, an optical characteristic measuring method for measuring the characteristics of devices under test having the first optical transmission line for letting light through only in one direction and the second optical transmission line for letting light through only in the direction opposite to the one direction includes: a fixed wavelength light generating step for generating a fixed wavelength light, the wavelength of which is fixed; a first light modulating step for introducing into the first optical transmission line the first incident light obtained by modulating the fixed wavelength light by the frequency of the electrical signals inputted; a first optical/electrical converting step for converting by the optical/electrical conversion process the first outgoing light having penetrated the first optical transmission line; a variable wavelength light generating step for generating a variable wavelength light, the wavelength of which is variable; a signal generating step for generating reference electrical signals of given frequencies; a second light modulating step for introducing onto the second optical transmission line the second incident light obtained by modulating the variable wavelength light by the frequency of the reference electrical signals; and a second optical/electrical converting step for converting by the optical/electrical conversion process the second outgoing light having penetrated the second optical transmission line and for outputting the converted second outgoing light onto the first light modulating step.

According to a fifteenth embodiment, an optical characteristic measuring method for measuring the characteristics of devices under test having the first optical transmission line letting light through only in one direction and the second optical transmission line letting light through only in the direction opposite to the one direction includes: a first variable wavelength light generating step for generating the first variable wavelength light, the wavelength of which is variable; a first light modulating step for introducing onto the first optical transmission line the first incident light obtained by modulating the first variable wavelength light by the frequency of electrical signals inputted; a first optical/electrical converting step for converting by the optical/electrical conversion process the first outgoing light having penetrated the first optical transmission line; a second variable wavelength light generating step for generating the second variable wavelength light, the wavelength of which is variable; a signal generating step for generating reference electrical signals of given frequencies; a second light modulating step for introducing into the second optical transmission line the second incident light obtained by modulating the second variable wavelength light by the frequency of the reference electrical signals; and a second optical/electrical converting step for converting by the optical/electrical conversion process the second outgoing light having penetrated the second optical transmission line and for outputting the converted second outgoing light onto the first light modulating step.

According to a sixteenth embodiment, a light generating method used in a method for measuring the characteristics of devices under test having the first optical transmission line letting light through only in one direction and the second optical transmission line letting light through only on the direction opposite to the one direction includes: a variable wavelength light generating step for generating a variable wavelength light, the wavelength of which is variable; a first light modulating step for introducing into the first optical transmission line the first incident light obtained by modulating the variable wavelength light by the frequency of electrical signals inputted; and a second optical/electrical converting step for converting by the optical/electrical conversion process the second outgoing light having penetrated the second optical transmission line and for outputting the converted second outgoing light onto the first light modulating step.

According to a seventeenth embodiment, an optical characteristic measuring method for measuring the characteristics of devices under test having a first optical transmission line letting light through only in one direction and a second optical transmission line letting light through only in the direction opposite to the one direction includes: a first optical/electrical converting step for converting by the optical/electrical conversion process the first incident light having penetrated the first optical transmission line; a fixed wavelength light generating step for generating a fixed wavelength light, the wavelength of which is fixed; a signal generating step for generating reference electrical signals of given frequencies; and a second light modulating step for introducing into the second optical transmission line the second incident light obtained by modulating the fixed wavelength light by the frequency of the reference electrical signals.

According to a eighteenth embodiment, a light generating method used in a measuring method of the characteristics of devices under test having the first optical transmission line letting light through only in one direction and the second optical transmission line letting light through only in the direction opposite to the one direction includes: a fixed wavelength light generating step for generating a fixed wavelength light, the wavelength of which is fixed; a first light modulating step for introducing into the first optical transmission line the first incident light obtained by modulating the fixed wavelength light by the frequency of electrical signals inputted; and a second optical/electrical converting step for converting by the optical/electrical conversion process the second outgoing light having penetrated the second optical transmission line and for outputting the converted second outgoing light onto the first light modulating step.

According to a nineteenth embodiment, an optical characteristic measuring method for measuring the characteristics of devices under test having the first optical transmission line letting light through only in one direction and the second optical transmission line letting light through only in the direction opposite to the one direction includes: a first optical/electrical converting step for converting by the optical/electrical conversion process the first outgoing light having penetrated the first optical transmission line; a variable wavelength light generating step for generating a variable wavelength light, the wavelength of which is variable; a signal generating step for generating reference electrical signals of given frequencies; a second light modulating step for introducing into the second optical transmission line the second incident light obtained by modulating the variable wavelength light by the frequency of the reference electrical signals.

According to a twentieth embodiment, a light generating method used in a measuring method of the characteristics of devices under test having the first optical transmission line letting light through only in one direction and the second optical transmission line letting light through only in the direction opposite to the one direction includes: a first variable wavelength light generating step for generating the first variable wavelength light, the wavelength of which is variable; a first light modulating step for introducing into the first optical transmission line the first incident light obtained by modulating the first variable wavelength light by the frequency of electrical signals inputted; and a second optical/electrical converting step for converting by the optical/electrical conversion process the second outgoing light having penetrated the second optical transmission line and for outputting the converted second outgoing light onto the first light modulating step.

A twenty-first embodiment includes an optical characteristic measuring method for measuring the characteristics of devices under test having the first optical transmission line letting light through only in one direction and the second optical transmission line letting light through only in the direction opposite to the one direction including: a first optical/electrical converting step for converting by the optical/electrical conversion process the first outgoing light having penetrated the first optical transmission line; a second variable wavelength light generating step for generating the second variable wavelength light, the wavelength of which is variable; a signal generating step for generating reference electrical signals of given frequencies; a second light modulating step for introducing into the second optical transmission line the second incident light obtained by modulating the second variable wavelength light by the frequency of the reference electrical signals.

A twenty-second embodiment includes a computer-readable medium having a program of instructions for execution by the computer to perform an optical characteristic measuring process for measuring the characteristics of devices under test having the first optical transmission line letting light through in one direction only and the second optical transmission line letting light through only on the direction opposite to the aforementioned direction, the optical characteristic measuring process including: a variable wavelength light generating processing for generating a variable wavelength light, the wavelength of which is variable; a first light modulating processing for introducing into the first optical transmission line the first incident light obtained by modulating the variable wavelength light by the frequency of the electrical signal inputted; a first optical/electrical converting processing for converting by the optical/electrical conversion process the first incident light having penetrated the first optical transmission line; a fixed wavelength light generating processing for generating a fixed wavelength light, the wavelength of which is fixed; a signal generating processing for generating reference electrical signals of given frequencies; a second light modulating processing for injecting into the second optical transmission line the second incident light obtained by modulating the fixed wavelength light by the frequency of the reference electrical signals; and a second optical/electrical converting processing for converting by the optical/electrical conversion process the second outgoing light having penetrated the second optical transmission line; and for outputting the converted second outgoing light onto the first light modulating processing.

A twenty-third embodiment includes a computer-readable medium having a program of instructions for execution by the computer to perform an optical characteristic measuring process for measuring the characteristics of devices under test having the first optical transmission line for letting light through only in one direction and the second optical transmission line for letting light through only in the direction opposite to the one direction, the optical characteristic measuring process including: a fixed wavelength light generating processing for generating a fixed wavelength light, the wavelength of which is fixed; a first light modulating processing for introducing into the first optical transmission line the first incident light obtained by modulating the fixed wavelength light by the frequency of the electrical signals inputted; a first optical/electrical converting processing for converting by the optical/electrical conversion process the first outgoing light having penetrated the first optical transmission line; a variable wavelength light generating processing for generating a variable wavelength light, the wavelength of which is variable; a signal generating processing for generating reference electrical signals of given frequencies; a second light modulating processing for introducing onto the second optical transmission line the second incident light obtained by modulating the variable wavelength light by the frequency of the reference electrical signals; and a second optical/electrical converting processing for converting by the optical/electrical conversion process the second outgoing light having penetrated the second optical transmission line and for outputting the converted second outgoing light onto the first light modulating processing.

A twenty-fourth embodiment includes a computer-readable medium having a program of instructions for execution by the computer to perform an optical characteristic measuring process for measuring the characteristics of devices under test having the first optical transmission line letting light through only in one direction and the second optical transmission line letting light through only in the direction opposite to the one direction, the optical characteristic measuring process including: a first variable wavelength light generating processing for generating the first variable wavelength light, the wavelength of which is variable; a first light modulating processing for introducing onto the first optical transmission line the first incident light obtained by modulating the first variable wavelength light by the frequency of electrical signals inputted; a first optical/electrical converting processing for converting by the optical/electrical conversion process the first outgoing light having penetrated the first optical transmission line; a second variable wavelength light generating processing for generating the second variable wavelength light, the wavelength of which is variable; a signal generating processing for generating reference electrical signals of given frequencies; a second light modulating processing for introducing into the second optical transmission line the second incident light obtained by modulating the second variable wavelength light by the frequency of the reference electrical signals; and a second optical/electrical converting processing for converting by the optical/electrical conversion process the second outgoing light having penetrated the second optical transmission line and for outputting the converted second outgoing light onto the first light modulating processing.

A twenty-fifth embodiment includes a computer-readable medium having a program of instructions for execution by the computer to perform a light generating process used in a process for measuring the characteristics of devices under test having the first optical transmission line letting light through only in one direction and the second optical transmission line letting light through only on the direction opposite to the one direction, the light generating process including: a variable wavelength light generating processing for generating a variable wavelength light, the wavelength of which is variable; a first light modulating processing for introducing into the first optical transmission line the first incident light obtained by modulating the variable wavelength light by the frequency of electrical signals inputted; and a second optical/electrical converting processing for converting by the optical/electrical conversion process the second outgoing light having penetrated the second optical transmission line and for outputting the converted second outgoing light onto the first light modulating processing.

A twenty-sixth embodiment includes a computer-readable medium having a program of instructions for execution by the computer to perform an optical characteristic measuring process for measuring the characteristics of devices under test having a first optical transmission line letting light through only in one direction and a second optical transmission line letting light through only in the direction opposite to the one direction, the optical characteristic measuring process including: a first optical/electrical converting processing for converting by the optical/electrical conversion process the first incident light having penetrated the first optical transmission line; a fixed wavelength light generating processing for generating a fixed wavelength light, the wavelength of which is fixed; a signal generating processing for generating reference electrical signals of given frequencies; and a second light modulating processing for introducing into the second optical transmission line the second incident light obtained by modulating the fixed wavelength light by the frequency of the reference electrical signals.

A twenty-seventh embodiment includes a computer-readable medium having a program of instructions for execution by the computer to perform a light generating process used in a measuring process of the characteristics of devices under test having the first optical transmission line letting light through only in one direction and the second optical transmission line letting light through only in the direction opposite to the one direction, the light generating process including: a fixed wavelength light generating processing for generating a fixed wavelength light, the wavelength of which is fixed; a first light modulating processing for introducing into the first optical transmission line the first incident light obtained by modulating the fixed wavelength light by the frequency of electrical signals inputted; and a second optical/electrical converting processing for converting by the optical/electrical conversion process the second outgoing light having penetrated the second optical transmission line and for outputting the converted second outgoing light onto the first light modulating processing.

A twenty-eight embodiment includes a computer-readable medium having a program of instructions for execution by the computer to perform an optical characteristic measuring process for measuring the characteristics of devices under test having the first optical transmission line letting light through only in one direction and the second optical transmission line letting light through only in the direction opposite to the one direction, the optical characteristic measuring process including: a first optical/electrical converting processing for converting by the optical/electrical conversion process the first outgoing light having penetrated the first optical transmission line; a variable wavelength light generating processing for generating a variable wavelength light, the wavelength of which is variable; a signal generating processing for generating reference electrical signals of given frequencies; a second light modulating processing for introducing into the second optical transmission line the second incident light obtained by modulating the variable wavelength light by the frequency of the reference electrical signals.

A twenty-ninth embodiment includes a computer-readable medium having a program of instructions for execution by the computer to perform a light generating process used in a measuring process of the characteristics of devices under test having the first optical transmission line letting light through only in one direction and the second optical transmission line letting light through only in the direction opposite to the one direction, the light generating process including: a first variable wavelength light generating processing for generating the first variable wavelength light, the wavelength of which is variable; a first light modulating processing for introducing into the first optical transmission line the first incident light obtained by modulating the first variable wavelength light by the frequency of electrical signals inputted; and a second optical/electrical converting processing for converting by the optical/electrical conversion process the second outgoing light having penetrated the second optical transmission line and for outputting the converted second outgoing light onto the first light modulating processing.

A thirtieth embodiment includes a computer-readable medium having a program of instructions for execution by the computer to perform an optical characteristic measuring process for measuring the characteristics of devices under test having the first optical transmission line letting light through only in one direction and the second optical transmission line letting light through only in the direction opposite to the one direction, the optical characteristic measuring process including: a first optical/electrical converting processing for converting by the optical/electrical conversion process the first outgoing light having penetrated the first optical transmission line; a second variable wavelength light generating processing for generating the second variable wavelength light, the wavelength of which is variable; a signal generating processing for generating reference electrical signals of given frequencies; a second light modulating processing for introducing into the second optical transmission line the second incident light obtained by modulating the second variable wavelength light by the frequency of the reference electrical signals.

DESCRIPTION OF THE PREFERRED EMBODIMENTS

The preferred embodiments of the present invention are described below with reference to the drawings.

The First Preferred Embodiment

Figure 1:
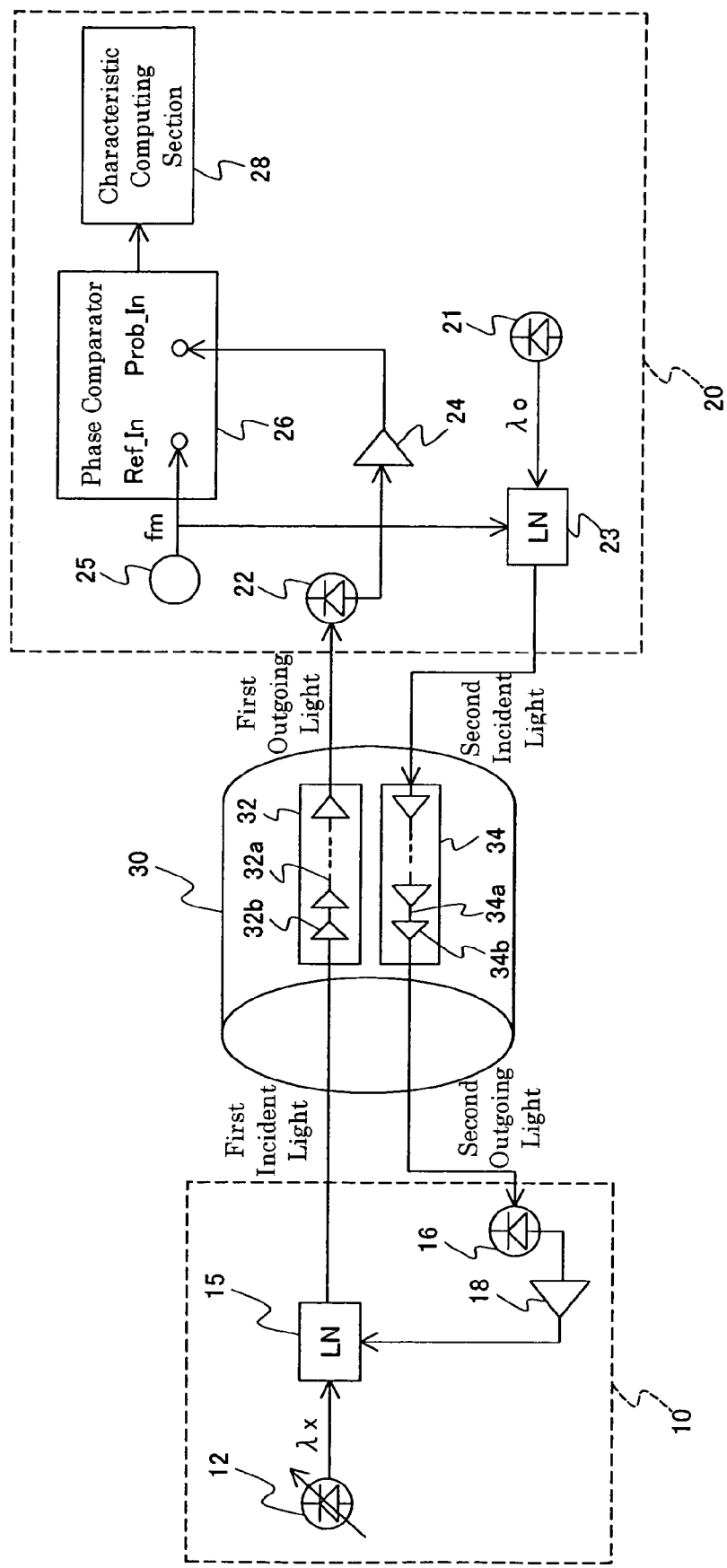
FIG. 1 is a block diagram showing the configuration of an optical characteristic measuring apparatus related to the first preferred embodiment of the present invention.

FIG. 1 is a block diagram showing the configuration of an optical characteristic measuring apparatus related to the first preferred embodiment of the present invention. The optical characteristic measuring apparatus related to the first preferred embodiment includes a light source system 10 connected to an end of a fiber pair 30 and a characteristic measuring system 20 connected to another end of the fiber pair 30.

A fiber pair 30 includes a first optical fiber transmission line 32 and a second optical fiber transmission line 34. The optical fiber transmission line 32 includes an optical fiber 32a and an optical amplifier 32b that amplifies light and is connected to the midway of the optical fiber 32a. The optical fiber transmission line 32 lets light through to the right. The optical fiber transmission line 34 includes an optical fiber 34a and an optical amplifier 34b that amplifies light and is connected to the midway of the optical fiber 34a. The optical fiber transmission line 34 lets light through to the left.

In the first preferred embodiment, the measurement of the first optical fiber transmission line 32 is assumed, and the light source system 10 is connected to the input (left) side of the first optical fiber transmission line 32 and the characteristic measuring system 20 is connected to the output (right) side.

The light source system 10 includes a variable wavelength light source 12, a first light modulator 15, a second optical/electrical converter 16 and an amplifier 18. The variable wavelength light source 12 generates a variable wavelength light, the wavelength of which is variable. The variable wavelength light source 12 can sweep the wavelength λ x of the variable wavelength light. The first light modulator 15 modulates the variable wavelength light by the frequency of electrical signals outputted by the second optical/electrical converter 16. The first light modulator 15 normally contains lithium niobate (LN), but it can dispense with LN provided that it can modulate. The light outputted by the first light modulator (the first incident light) is inputted into the first optical fiber transmission line 32. The second optical/electrical converter 16 converts by the optical/electrical conversion process the second outgoing light outputted from the second optical fiber transmission line 34. The amplifier 18 amplifies the electrical signals outputted by the second optical/electrical converter 16 and inputs them into the first light modulator 15.

The first incident light inputted into the first optical fiber transmission line 32 penetrates the first optical fiber transmission line 32. The light having penetrated the first optical fiber transmission line 32 is called as the first outgoing light.

The characteristic measuring system 20 includes a fixed wavelength light source 21 a first optical/electrical converter 22, a second light modulator 23, an amplifier 24, a power source (signal source) 25, a phase comparator 26 and a characteristic computing section 28.

The fixed wavelength light source 21 generates a fixed wavelength light, the wavelength of which is fixed. It is desirable to fix the wavelength of the fixed wavelength light at a wavelength $\lambda\,0$ at which the wavelength dispersion will be reduced to the minimum in the second optical fiber transmission line 34.

The first optical/electrical converter 22 converts the first outgoing light by the optical/electrical conversion process. The power source (signal source) 25 generates electrical signals of a frequency fm (reference electrical signals). The second light modulator 23 modulates the fixed wavelength light by the frequency fm of the electrical signals outputted by the power source (signals source) 25. The second light modulator 23 includes lithium niobate (LN). The light outputted by the second light modulator 23 (the second incident light) is inputted into the second optical fiber transmission line 34. Incidentally, the second incident light penetrates the second optical fiber transmission line 34. The light having penetrated the second optical fiber transmission line 34 is called as the second outgoing light. The amplifier 24 amplifies the output of the first optical/electrical converter 22.

The phase comparator 26 receives the electrical signals generated by the power source (signal source) 25 at a terminal Ref_In and the electrical signals outputted by the amplifier 24 at a terminal Prob_In. The phase comparator 26 takes the electrical signals received at the terminal Ref_In as a reference for computing the phase of the electrical signals received at the terminal Prob_In.

The characteristic computing section 28 records the phases measured by the phase comparator 26 and computes the group delay characteristic and the wavelength dispersion characteristic of the first optical fiber transmission line 32 based on the phases recorded. The group delay characteristic can be computed from the relationship between the phases measured by the phase comparator 26 and the modulation frequency fm. The wavelength dispersion characteristic can be computed by differentiating the group delay characteristic by the wavelength.

And now, the operation of the first preferred embodiment of the present invention will be described with reference to the flowchart in FIG. 2. On the left side the operation of the characteristic measuring system 20 is shown, and on the right side the operation of the light source system 10 is shown. Referring to the left side to begin with, the fixed wavelength light source 21 generates a fixed wavelength light ($\lambda=\lambda 0$) (S20). Then, the fixed wavelength light is modulated by the frequency fm of the reference electrical signals generated by the power source (signal source) (S22). And the process returns to the generation of the fixed wavelength light source (S20).

The fixed wavelength light modulated by the frequency fm is the second incident light. The second incident light penetrates the second optical fiber transmission line 34 and is inputted into the light source system 10 as the second outgoing light.

Figure 2:
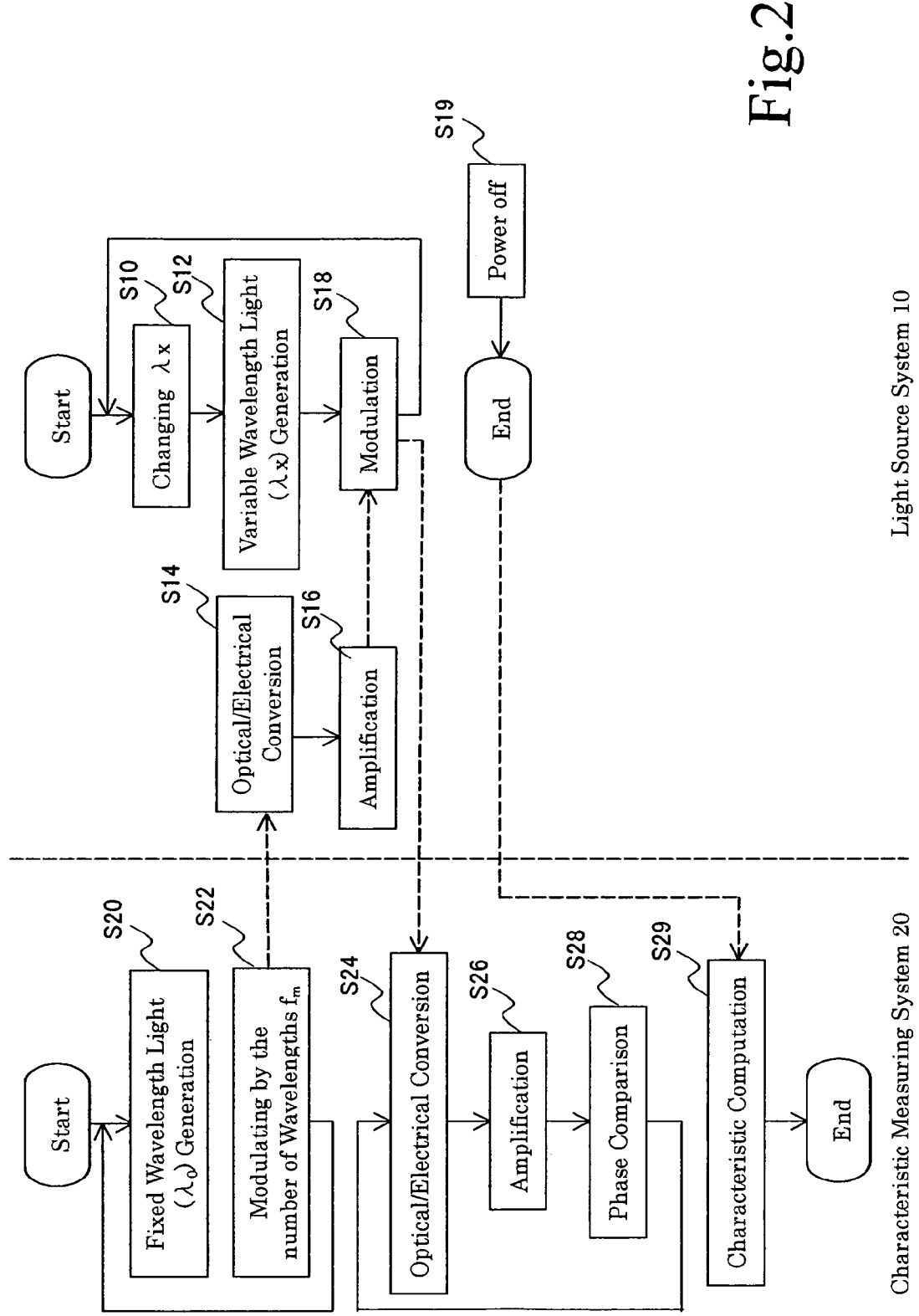
FIG. 2 is a flowchart showing the operation of the first preferred embodiment of the present invention.

At this point, let us refer to the right side of FIG. 2. The wavelength $\lambda\,x$ of the variable wavelength light is changed (S10). Then, the variable wavelength light source 12 generates a variable wavelength light ($\lambda=\lambda x$) (S12). The second outgoing light is converted by the optical/electrical conversion process by the second optical/electrical converter 16 (S14).

Here, the wavelength $\lambda\,0$ of the fixed wavelength light is set in such a way that the wavelength dispersion may be reduced to the minimum in the second optical fiber transmission line 34. Therefore, the result of the optical/electrical conversion of the second outgoing light has a smaller phase difference than that of the second incident light. Thus, the result of the optical/electrical conversion of the second outgoing light and the reference electrical signals can be considered to have the identical frequencies and phases.

And the output of the second optical/electrical converter 16 is amplified by the amplifier 18 (S16). Then, the variable wavelength light is modulated by the first light modulator 15 by the frequency of the electrical signals outputted by the second optical/electrical converter 16 (S18). The frequency of the electrical signals outputted by the second optical/electrical converter 16 can be considered to be equal to the frequency fm of the reference electrical signals. In the meanwhile, the light modulated by the first light modulator 15 (the first incident light) is inputted into the first optical fiber transmission line 32.

And now, the process returns to the change (sweep) of the wavelength $\lambda\,x$ of the variable wavelength light (S10). And the operation is terminated by switching off the power at any time (S19).

Then, let us refer to the left of FIG. 2. The first incident light penetrates the first optical fiber transmission line 32 and becomes the first outgoing light. The first outgoing light is converted by the optical/electrical conversion process by the first optical/electrical converter 22 (S24). The electrical signals outputted by the first optical/electrical converter 22 is amplified by the amplifier 24 (S26). Then, the phase comparator 26 receives the reference electrical signals generated by the power source (signal source) 25 at its terminal Ref_In and the electrical signals for measurement outputted by the amplifier 24 at its terminal Prob_In. The phase comparator 26 takes the electrical signals received at the terminal Ref_In as a reference for computing the phase of the electrical signals received at the terminal Prob_In (S28). And the phases measured are recorded at the characteristic computing section 28.

And the phases of the electrical signals for measurement received at the terminal Prob_In are affected by wavelength dispersion by the first optical fiber transmission line 32. But, the phase of the reference electrical signals received at the terminal Ref_In are not affected by the wavelength dispersion by the first optical fiber transmission line 32. Thus, the measurement of the phases of the electrical signals for measurement received at the terminal Prob_In by taking the reference electrical signals received at the term Ref_In as references enables to compute the characteristics of the first optical fiber transmission line 32.

When the light source system 10 stops operating, the characteristic computing section 28 computes the group delay characteristic and the wavelength dispersion characteristic of the first optical fiber transmission line 32 (S29).

The group delay characteristic can be computed from the relationship between the phases measured by the phase comparator 26 and the modulation frequency fm. The wavelength dispersion characteristic can be computed by differentiating the group delay characteristic by the wavelength.

According to the first preferred embodiment, it is possible to measure the wavelength dispersion of the first optical fiber transmission line 32 even if only one fiber pair can be secured.

The Second Preferred Embodiment

The optical characteristic measuring apparatus related to the second preferred embodiment is different from the first preferred embodiment in that the characteristic measuring system 20 has a variable wavelength light source and that the characteristic measuring system 20 converts by the optical/electrical conversion process and amplifies the reverberation of the second incident light and compares the phases with those of the reference electrical signals.

Figure 3:
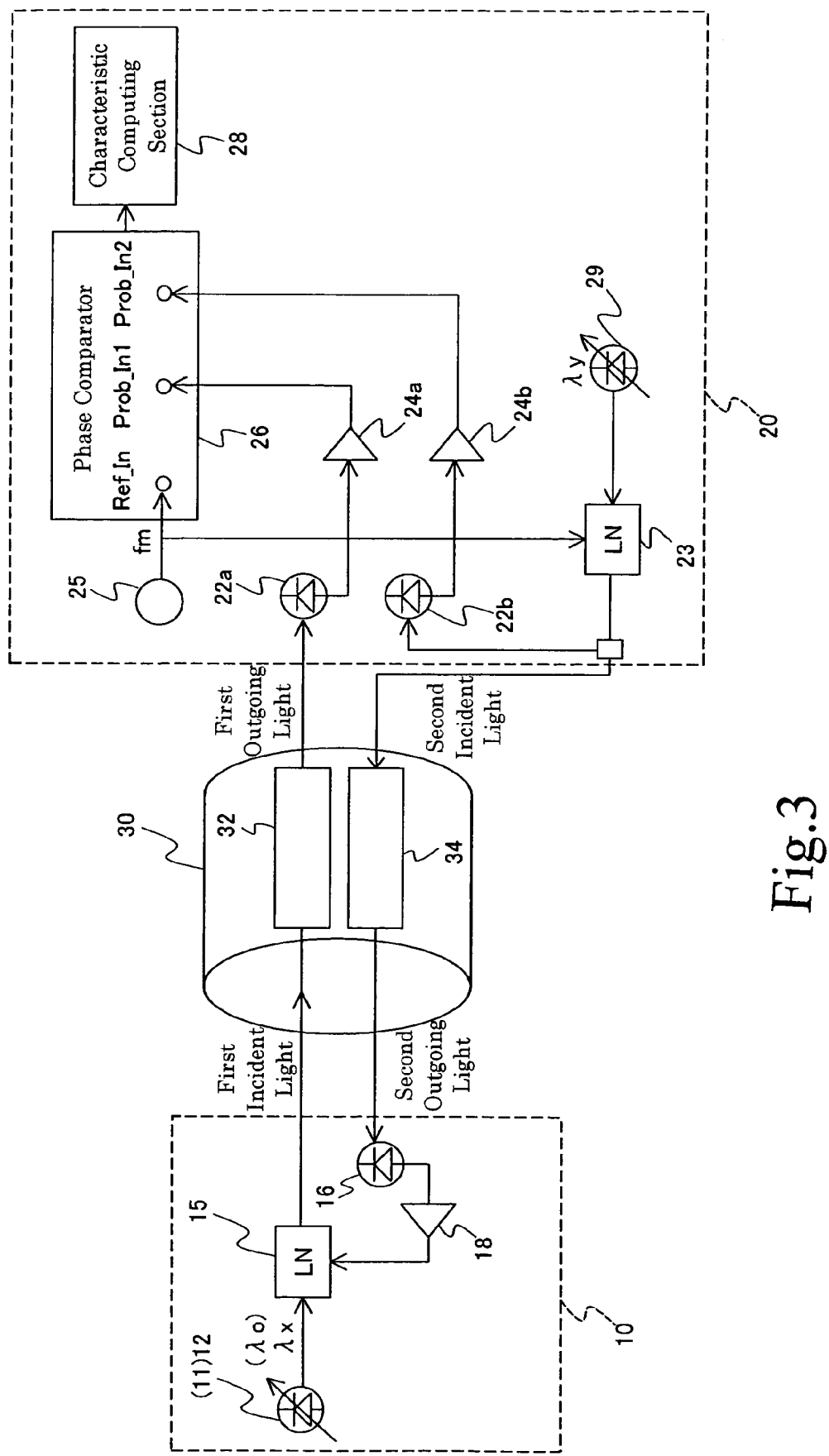
FIG. 3 is a block diagram showing the configuration of an optical characteristic measuring apparatus related to the second and third preferred embodiments of the present invention.

FIG. 3 is a block diagram showing the summarized configuration of an optical characteristic measuring apparatus related to the second preferred embodiment. Hereafter, the portions similar to the first preferred embodiment will be marked by the codes of similarity and their descriptions will be omitted.

The light source system 10 includes a fixed wavelength light source 11, a first light modulator 15, a second optical/electrical converter 16 and an amplifier 18. The fixed wavelength light source 11 generates a fixed wavelength light, the wavelength of which is fixed. It is preferable to set the wavelength of the fixed wavelength light at a wavelength $\lambda 0$ at which the wavelength dispersion will be reduced to the minimum in the first optical fiber transmission line 32.

The characteristic measuring system 20 includes a variable wavelength light source 29, a first optical/electrical converter 22a, a third optical/electrical converter 22b, a second light modulator 23, amplifiers 24a and b, a power source (signal source) 25, a phase comparator 26 and a characteristic computing section 28.

The variable wavelength light source 29 generates a variable wavelength light, the wavelength of which is variable. The variable wavelength light source 21 can sweep the wavelength $\lambda$ y of the variable wavelength light. The third optical/electrical converter 22b converts by the optical/electrical conversion process the reverberations of the second incident light. The amplifier 24b amplifies the electrical signals outputted by the third optical/electrical converter 22b.

The phase comparator 26 receives the electrical signals generated by the power source (signal source) 25 at a terminal Ref_In, the electrical signals outputted by the amplifier 24a at a terminal Prob_In 1 and the electrical signals for the measurement of reverberations outputted by the amplifier 24b at a terminal Prob_In 2. The phase comparator 26 takes the electrical signals received at the terminal Ref_In as a reference for computing the phase of the electrical signals received at the terminal Prob_In 1 and the terminal Prob_In 2.

The operation of the second preferred embodiment will be described with reference to the flowchart in FIG. 4. On the left side the operation of the characteristic measuring system 20 is shown, while on the right side the operation of the light source system 10 is shown. Let us refer to the left side to begin with. The wavelength $\lambda$ y of the variable wavelength light is changed (S20). Then, the variable wavelength light source 12 generates a variable wavelength light ($\lambda=\lambda$y) (S21). Then, the variable wavelength light is modulated by the frequency fin of the reference electrical signals generated by the power source (signal source) (S22). And then the process returns to the generation of the variable wavelength light (S20).

The fixed wavelength light modulated by the frequency fin is the second incident light. The second incident light penetrates the second optical fiber transmission line 34 and is inputted into the light source system 10 as the second outgoing light.

Figure 4:
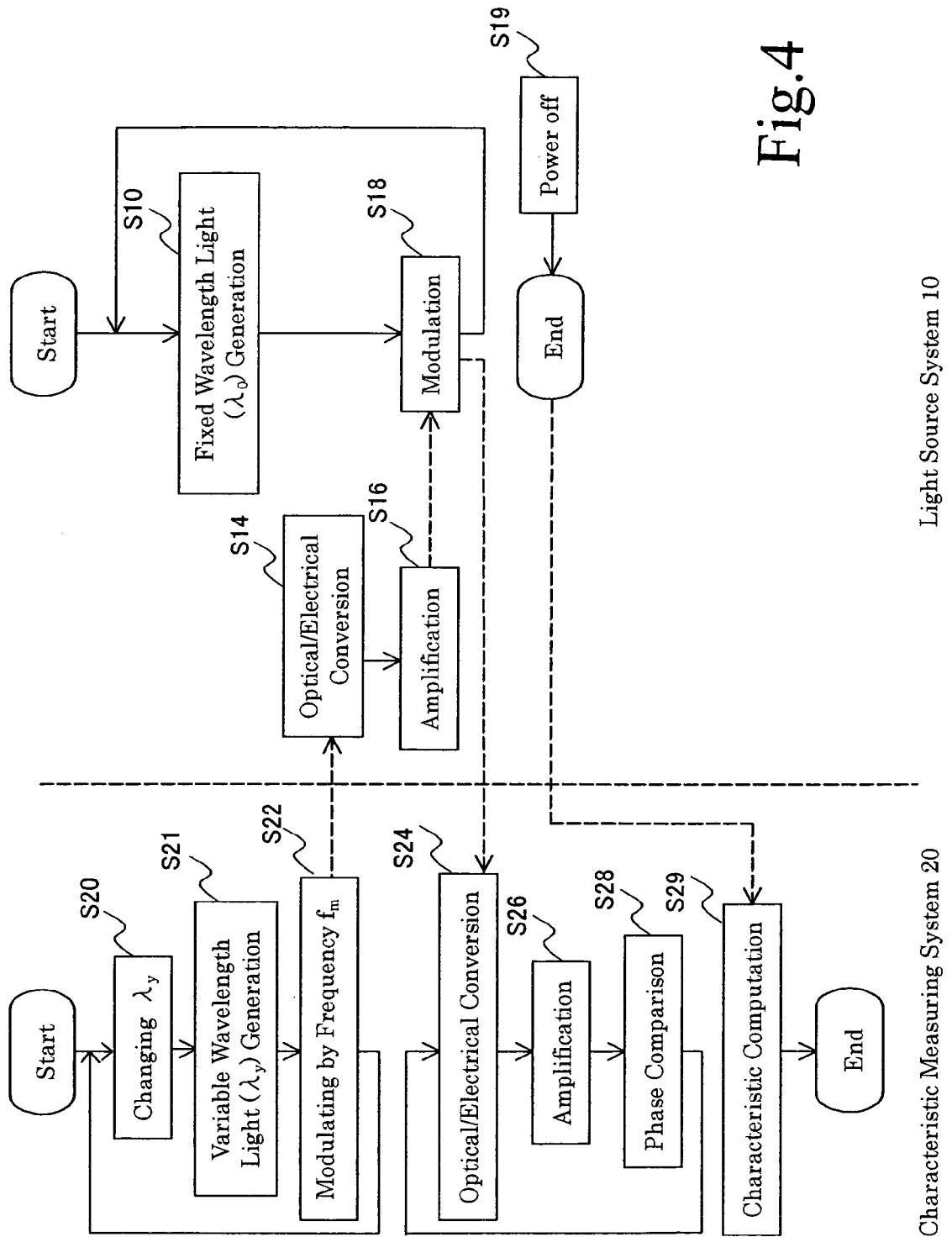
FIG. 4 is a flowchart showing the operation of the second preferred embodiment of the present invention.

At this point, let us refer to the right side of FIG. 4. To begin with, the fixed wavelength light source 21 generates a fixed wavelength light ($\lambda=\lambda 0$) (S10). The second outgoing light is converted by the optical/electrical conversion process by the second optical/electrical converter 16 (S14).

Here, the result of optical/electrical conversion of the second outgoing light is affected by the wavelength dispersion of the second optical fiber transmission line 34.

And the output of the second optical/electrical converter 16 will be amplified (S16). Then, the variable wavelength light will be modulated by the first optical/electrical converter 15 by the frequency of the electrical signals outputted by the second optical/electrical converter 16 (S18). In the meanwhile, the light modulated by the first light modulator 15 (the first incident light) will be injected into the first optical fiber transmission line 32.

Here, the wavelength $\lambda$ 0 of the fixed wavelength light is set in such a way that the wavelength dispersion may be reduced to the minimum in the first optical fiber transmission line 32. Thus, the result of the optical/electrical conversion of the first outgoing light is not affected by the wavelength dispersion of the first optical fiber transmission line 32 and is affected only by the wavelength dispersion of the second optical fiber transmission line 34.

And the process returns to the generation of the fixed wavelength light (S10). In the meanwhile, the whole operation is terminated by switching off the power at any time (S19).

Then, let us refer to the left of FIG. 4. The first incident light penetrates the first optical fiber transmission line 32 and becomes the first outgoing light. The first outgoing light is converted by the optical/electrical conversion process by the first optical/electrical converter 22a (S24). And the third optical/electrical converter 22b converts by the optical/electrical conversion process the reverberations of the second incident light (S24). Then, the electrical signals outputted by the first optical/electrical converter 22a and the third optical/electrical converter 22b are respectively amplified by the amplifiers 24a and b (S26). Then, the phase comparator 26 receives the reference electrical signals generated by the power source (signal source) 25 at its terminal Ref_In, the electrical signals for measurement outputted by the amplifier 24a at its terminal Prob_In 1 and the electrical signals for measurement of reverberations outputted by the amplifier 24b at its terminal Prob_In 2. The phase comparator 26 takes the electrical signals received at the terminal Ref_In as a reference for computing the phase of the electrical signals received at the terminals Prob_In 1 and Prob_In 2 (S28). And the phases measured are recorded at the characteristic computing section 28.

And the phases of the electrical signals received at the terminals Prob_In 1 and Prob_In 2 are affected by wavelength dispersion by the second optical fiber transmission line 34. But, the phase of the reference electrical signals received at the terminal Ref_In is not affected by wavelength dispersion by the second optical fiber transmission line 34. Thus, the measurement of the phases of the electrical signals received at the terminals Prob_In 1 and Prob_In 2 by taking the reference electrical signals received at the term Ref_In as references enables to compute the characteristics of the second optical fiber transmission line 34.

When the light source system 10 stops operating, the characteristic computing section 28 computes the group delay characteristic and the wavelength dispersion characteristic of the first optical fiber transmission line 32 (S29). The group delay characteristic can be computed from the relationship between the phases measured by the phase comparator 26 and the modulation frequency fin. The wavelength dispersion characteristic can be computed by differentiating the group delay characteristic by the wavelength.

According to the second preferred embodiment, it is possible to measure the wavelength dispersion of the second optical fiber transmission line 34 even if only one fiber pair can be secured.

The Third Preferred Embodiment

The optical characteristic measuring apparatus related to the third preferred embodiment is different from the second preferred embodiment in that the light source system 10 has a variable wavelength light source.

The configuration of the third preferred embodiment is described with reference to FIG. 3. The light source system 10 includes a variable wavelength light source 12, a first light modulator 15, a second optical/electrical converter 16 and an amplifier 18. The first variable wavelength light source 12 generates the first variable wavelength light, the wavelength of which is variable. The first variable wavelength light source 12 enables to sweep the wavelength λ x of the first variable wavelength light. The configuration of other parts is similar to that of the second preferred embodiment. Also the configuration of the characteristic measuring system 20 is similar to that of the second preferred embodiment. However, the variable wavelength light source 21 in the second preferred embodiment is replaced by the second variable wavelength light source 21 in the third preferred embodiment.

The operation of the third preferred embodiment will be described with reference to the flowchart in FIG. 5. On the left side the operation of the characteristic measuring system 20 is shown, while on the right side the operation of the light source system 10 is shown. Let us refer to the left side to begin with. The wavelength λ y of the second variable wavelength light is changed (S20). Then, the variable wavelength light source 12 generates the second variable wavelength light (λ=λy) (S21). Then, the second variable wavelength light is modulated by the frequency fin of the reference electrical signals generated by the power source (signal source) (S22). And then the process returns to the generation of the second variable wavelength light (S20).

The fixed wavelength light modulated by the frequency fin is the second incident light. The second incident light penetrates the second optical fiber transmission line 34 and is inputted into the light source system 10 as the second outgoing light.

Figure 5:
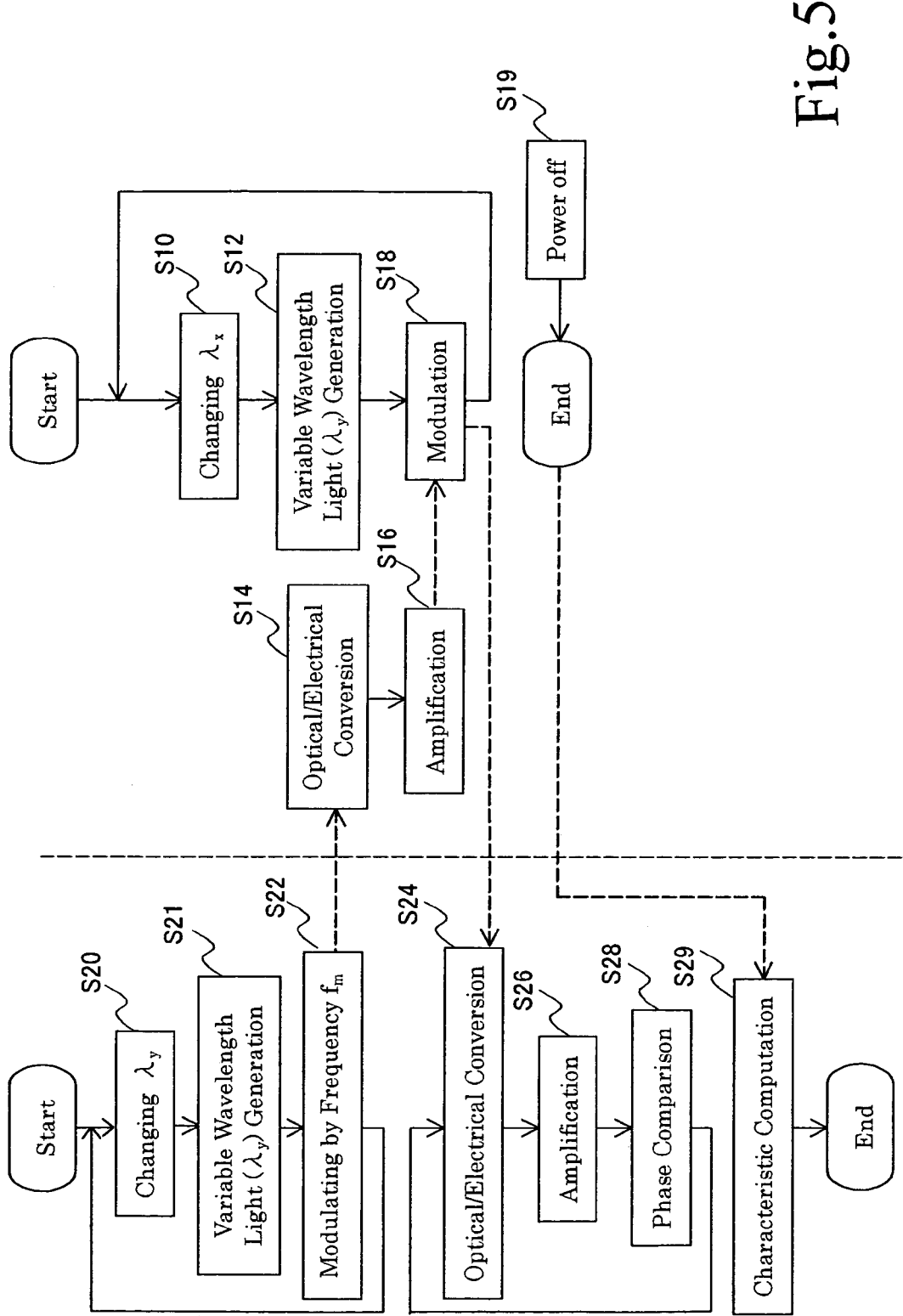
FIG. 5 is a flowchart showing the operation of the third preferred embodiment of the present invention.
Figure 6A:
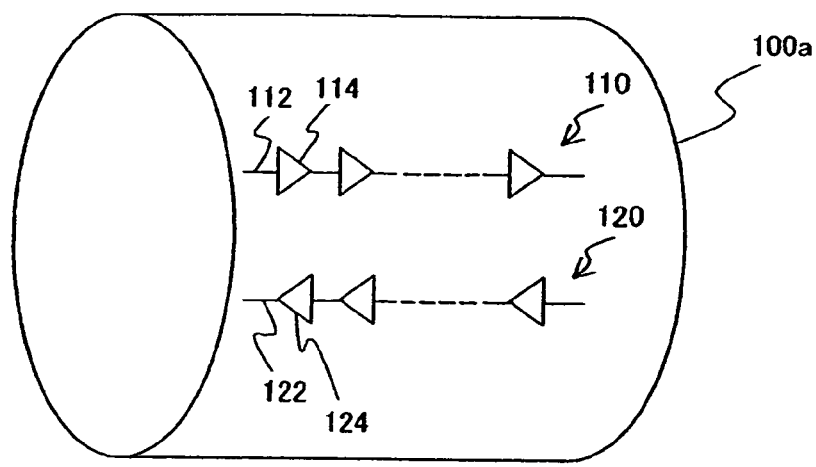
FIGS. 6(a) and 6(b) are illustrations showing the structure of a fiber pair according to the prior art.
Figure 6B:
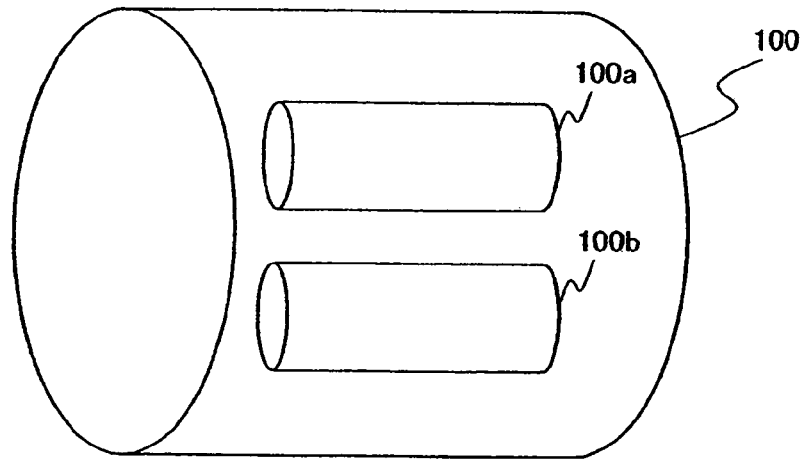
Figure 7:
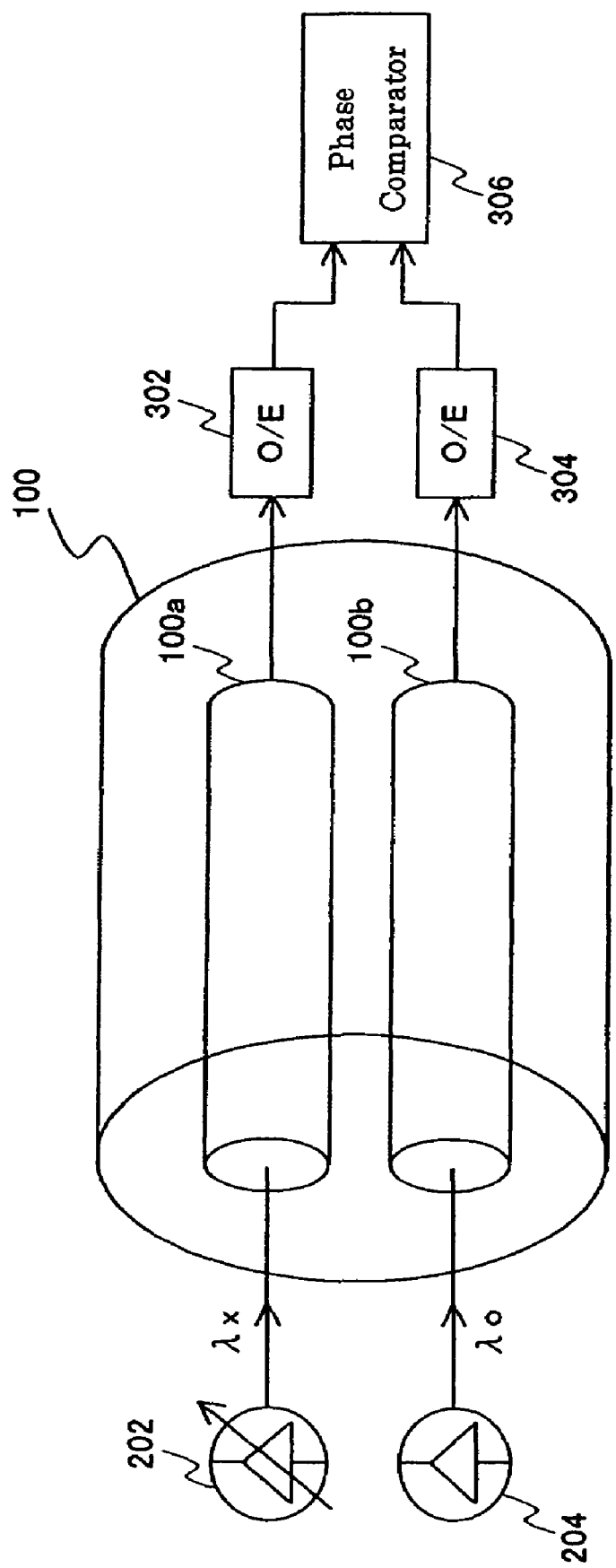
FIG. 7 is an illustration showing the configuration of the measuring system used to measure the wavelength dispersion characteristic of two fiber pairs according to the prior art.

At this point, let us refer to the right side of FIG. 5. The wavelength λ x of the first variable wavelength light is changed (S10). Incidentally, the change (sweep) of λ x and that of λ y will be synchronized. Then, the first variable wavelength light source 12 generates the first variable wavelength light (λ=λx) (S12). The second outgoing light is converted by the optical/electrical conversion process by the second optical/electrical converter 16 (S14).

And the output of the second optical/electrical converter 16 will be amplified (S16). Then, the first variable wavelength light will be modulated by the first light modulator 15 by the frequency of the electrical signals outputted by the second optical/electrical converter 16 (S18). In the meanwhile, the light modulated by the first light modulator 15 (the first incident light) will be inputted into the first optical fiber transmission line 32.

And the process returns to the generation of the first variable wavelength light (S110). In the meanwhile, the whole operation is terminated by switching off the power at any time (S19).

Then, let us refer to the left of FIG. 5. The first incident light penetrates the first optical fiber transmission line 32 and becomes the first outgoing light. The first outgoing light is converted by the optical/electrical conversion process by the first optical/electrical converter 22a (S24). And the third optical/electrical converter 22b converts by the optical/electrical conversion process the reverberations of the second incident light (S24). Then, the electrical signals outputted by the first optical/electrical converter 22a and the third optical/electrical converter 22b are amplified by the amplifiers 24a and *b* (S26). Then, the phase comparator 26 receives the reference electrical signals generated by the power source (signal source) 25 at its terminal Ref_In, the electrical signals for measurement outputted by the amplifier 24a at its terminal Prob_In 1 and the electrical signals for measurement of reverberations outputted by the amplifier 24b at its terminal Prob_In 2. The phase comparator 26 takes the electrical signals received at the terminal Ref_In as a reference for computing the phase of the electrical signals received at the terminals Prob_In 1 and Prob_In 2 (S28). And the phases measured are recorded at the characteristic computing section 28.

When the light source system 10 stops operating, the characteristic computing section 28 computes the group delay characteristic and the wavelength dispersion characteristic of the first optical fiber transmission line 32 (S29). The group delay characteristic can be computed from the relationship between the phases measured by the phase comparator 26 and the modulation frequency fin. The wavelength dispersion characteristic can be computed by differentiating the group delay characteristic by the wavelength.

According to the third preferred embodiment, it is possible to measure the wavelength dispersion of the first optical fiber transmission line 32 and the second optical fiber transmission line 34 even if only one fiber pair can be secured.

In the meanwhile, the embodiment described above can be realized by having a media reading apparatus of a computer provided with a CPU, a hard disk, memory media (a floppy disk, a CD-ROM, etc.) read a program executing various functions described above and installing the program on a hard disk. In this way, the functions described above can be performed.

According to the present invention, it is possible to measure group delay characteristic and other characteristics even if the device under test is a single fiber pair.

What is claimed is:

1. An optical characteristic measuring apparatus for measuring characteristics of devices under test having a first optical transmission line letting light through only in a first direction and a second optical transmission line letting light through only in a second direction opposite to said first direction, said apparatus comprising:

a first variable wavelength light source for generating a first variable wavelength light;

a first light modulating element for introducing into said first optical transmission line a first incident light obtained by modulating said first variable wavelength light with a frequency of a first electrical signal, wherein said first incident light exits from said first optical transmission line as a first outgoing light;

a first optical/electrical converting element for converting by a first optical/electrical conversion process, the first outgoing light into a second electrical signal;

a second variable wavelength light source for generating a second variable wavelength light;

a signal source for generating a reference electrical signal;

a second light modulating element for introducing into the second optical transmission line a second incident light obtained by modulating said second variable wavelength light with said reference electrical signal, wherein said second incident light exits from said second optical transmission line as a second outgoing light;

a second optical/electrical converting element for converting, by a second optical/electrical conversion process, the second outgoing light into the first electrical signal and for outputting the first electrical signal into said first light modulating element; and a third optical/electrical converting element for converting, by a third optical/electrical conversion process, a reflected light, which is generated when said second light modulating element introduces said second incident light into said second optical transmission line, into a third electrical signal.

2. The optical characteristic measuring apparatus according to claim 1, further comprising:

a phase comparing element for measuring a phase difference between a phase of the second electrical signal output by said first optical/electrical converting element and a phase of said reference electrical signal; and a characteristic computing element for computing a group delay characteristic or a dispersion characteristic of the devices under test by using said phase difference.

3. The optical characteristic measuring apparatus according to claim 1, further comprising:

a phase comparing element for measuring a phase difference between a phase of the third electrical signal output by said third optical/electrical converting element and a phase of said reference electrical signal; and a characteristic computing element for computing a group delay characteristic or a dispersion characteristic of the devices under test by using said phase difference.

4. An optical characteristic measuring apparatus for measuring characteristics of devices under test having a first optical transmission line letting light through only in a first direction and a second optical transmission line letting light through only in a second direction opposite to said first direction, said apparatus comprising:

an optical/electrical converting element for converting, by an optical/electrical conversion process, an outgoing light, which has penetrated and exits from said first optical transmission line, into an electrical signal;

a variable wavelength light source for generating a variable wavelength light;

a signal source for generating a reference electrical signal;

a light modulating element for introducing into said second optical transmission line an incident light obtained by modulating said variable wavelength light with said reference electrical signal; and a further optical/electrical converting element for converting by a further optical/electrical conversion process, a reflected light, which is generated when said light modulating element introduces said incident light into said second optical transmission line, into a further electrical signal.

5. An optical characteristic measuring method of measuring characteristics of devices under test having a first optical transmission line letting light through only in a first direction and a second optical transmission line letting light through only in a second direction opposite to said first direction, said method comprising:

generating a first variable wavelength light;

introducing into said first optical transmission line a first incident light obtained by modulating said first variable wavelength light with a first electrical signal, wherein said first incident light exits from said first optical transmission line as a first outgoing light;

converting, by a first optical/electrical conversion process, the first outgoing light into a second electrical signal;

generating a second variable wavelength light;

generating a reference electrical signal;

introducing into the second optical transmission line a second incident light obtained by modulating said second variable wavelength light with said reference electrical signal, wherein said second incident light exits from said second optical transmission line as a second outgoing light;

converting, by a second optical/electrical conversion process, the second outgoing light and using the converted second outgoing light as the first electrical signal in the step of modulating said first variable wavelength light to obtain the first incident light; and converting, by a third optical/electrical conversion process, a reflected light, which is generated when said second incident light is introduced into said second optical transmission line, into a third electrical signal.

6. An optical characteristic measuring method of measuring characteristics of devices under test having a first optical transmission line letting light through only in a first direction and a second optical transmission line letting light through only in a second direction opposite to said first direction, said method comprising:

converting, by an optical/electrical conversion process, a first outgoing light, which has penetrated and exits from said first optical transmission line, into an electrical signal;

generating a variable wavelength light;

generating a reference electrical signal;

introducing into said second optical transmission line an incident light obtained by modulating said variable wavelength light with said reference electrical signal; and converting, by a further optical/electrical conversion process, a reflected light, which is generated when said incident light is introduced into said second optical transmission line, into a further electrical signal.

7. A computer-readable medium having a program of instructions for execution by a computer to perform an optical characteristic measuring process of measuring characteristics of devices under test having a first optical transmission line letting light through only in a first direction and a second optical transmission line letting light through only in a second direction opposite to said first direction, said optical characteristic measuring process comprising:

a first variable wavelength light generating processing for generating a first variable wavelength light;

a first light modulating processing for introducing into said first optical transmission line a first incident light obtained by modulating said first variable wavelength light with a first electrical signal, wherein the first incident light exits from said first optical transmission line as a first outgoing light;
  a first optical/electrical converting processing for converting, by a first optical/electrical conversion process, the first outgoing light into a second electrical signal;
  a second variable wavelength light generating processing for generating a second variable wavelength light;
  a signal generating processing for generating a reference electrical signal;
  a second light modulating processing for introducing into the second optical transmission line a second incident light obtained by modulating said second variable wavelength light with said reference electrical signal, wherein the second incident light exits from said second optical transmission line as a second outgoing light;
  a second optical/electrical converting processing for converting, by a second optical/electrical conversion process, the second outgoing light and using the converted second outgoing light as the first electrical signal in the step of modulating said first variable wavelength light to obtain the first incident light; and
  a third optical/electrical converting processing for converting, by a third optical/electrical conversion process, a reflected light which is generated when said second incident light is introduced into said second optical transmission line, into a third electrical signal.

8. A computer-readable medium having a program of instructions for execution by a computer to perform an optical characteristic measuring process of measuring characteristics of devices under test having a first optical transmission line letting light through only in a first direction and a second optical transmission line letting light through only in a second direction opposite to said first direction, said optical characteristic measuring process comprising:
  a first optical/electrical converting processing for converting, by an optical/electrical conversion process, a first outgoing light, which has penetrated and exits from said first optical transmission line, into an electrical signal;
  a second variable wavelength light generating processing for generating a variable wavelength light;
  a signal generating processing for generating a reference electrical signal;
  a second light modulating processing for introducing into said second optical transmission line an incident light obtained by modulating said variable wavelength light with said reference electrical signal; and
  a further optical/electrical converting processing for converting, by a further optical/electrical conversion process, a reflected light, which is generated when said incident light is introduced into said second optical transmission line, into a further electrical signal.

9. An optical characteristic measuring apparatus for measuring characteristics of devices under test having a first optical transmission line letting light through only in a first direction and a second optical transmission line letting light through only in a second direction opposite to said first direction, said apparatus comprising:
  a first variable wavelength light source for generating a first variable wavelength light;
  first light modulating means for introducing into said first optical transmission line a first incident light obtained by modulating said first variable wavelength light with a first electrical signal, wherein said first incident light exits from said first optical transmission line as a first outgoing light;
  first optical/electrical converting means for converting, by a first optical/electrical conversion process, the first outgoing light into a second electrical signal;
  a second variable wavelength light source for generating a second variable wavelength light;
  a signal source for generating a reference electrical signal;
  second light modulating means for introducing into the second optical transmission line a second incident light obtained by modulating said second variable wavelength light with said reference electrical signal, wherein said second incident light exits from said second optical transmission line as a second outgoing light;
  second optical/electrical converting means for converting, by a second optical/electrical conversion process, the second outgoing light into the first electrical signal and for outputting the first electrical signal into said first light modulating means; and
  third optical/electrical converting means for converting by a third optical/electrical conversion process, a reflected light, which is generated when said second light modulating means introduces said second incident light into said second optical transmission line, into a third electrical signal.

10. An optical characteristic measuring apparatus for measuring characteristics of devices under test having a first optical transmission line letting light through only in a first direction and a second optical transmission line letting light through only in a second direction opposite to said first direction, said apparatus comprising:
  optical/electrical converting means for converting, by an optical/electrical conversion process, an outgoing light, which has penetrated and exits from said first optical transmission line, into an electrical signal;
  a variable wavelength light source for generating a variable wavelength light;
  a signal source for generating a reference electrical signal;
  light modulating means for introducing into said second optical transmission line an incident light obtained by modulating said variable wavelength light with said reference electrical signal; and
  further optical/electrical converting means for converting, by a further optical/electrical conversion process, a reflected light, which is generated when said light modulating means introduces said incident light into said second optical transmission line, into a further electrical signal.

* * * * *